United States Patent [19]

Pagani et al.

[11] 4,291,006

[45] Sep. 22, 1981

[54] COMBINED PROCESS FOR THE PRODUCTION OF UREA AND AMMONIA

[75] Inventors: Giorgio Pagani; Vincenzo Lagana, both of Milan; Francesco Saviano, Segrate, all of Italy

[73] Assignee: Snamprogetti S.p.A, Milan, Italy

[21] Appl. No.: 59,217

[22] Filed: Jul. 20, 1979

Related U.S. Application Data

[63] Continuation of Ser. No. 880,139, Feb. 22, 1978, abandoned.

[51] Int. Cl.$^3$ .............................................. C01C 1/04
[52] U.S. Cl. .................................... 423/359; 564/66; 564/67; 564/69
[58] Field of Search ............... 423/359, 360, 361, 362, 423/363; 260/555 A, 555 R; 564/66, 67, 68, 69

[56] References Cited

U.S. PATENT DOCUMENTS

| | | |
|---|---|---|
| 3,573,173 | 3/1971 | Otsuka et al. .................. 260/555 A |
| 3,684,442 | 8/1972 | Konoki et al. .................. 260/555 A |
| 4,013,718 | 3/1977 | Guadalupi et al. ............. 260/555 A |

Primary Examiner—Edward J. Meros
Assistant Examiner—Wayne A. Langel
Attorney, Agent, or Firm—Morgan, Finnegan, Pine, Foley & Lee

[57] ABSTRACT

In an integrated or combined process for the production of ammonia and urea, the improvement consisting in that the absorption of $CO_2$ from the raw gas going to the synthesis reactor for ammonia is carried out with an absorption apparatus which is divided into two sections, one being of the plate type and the other of the thin film type. The predominant fraction of $CO_2$ is stripped in the thin-film section, the remainder in the adiabatic plate section.

7 Claims, 1 Drawing Figure

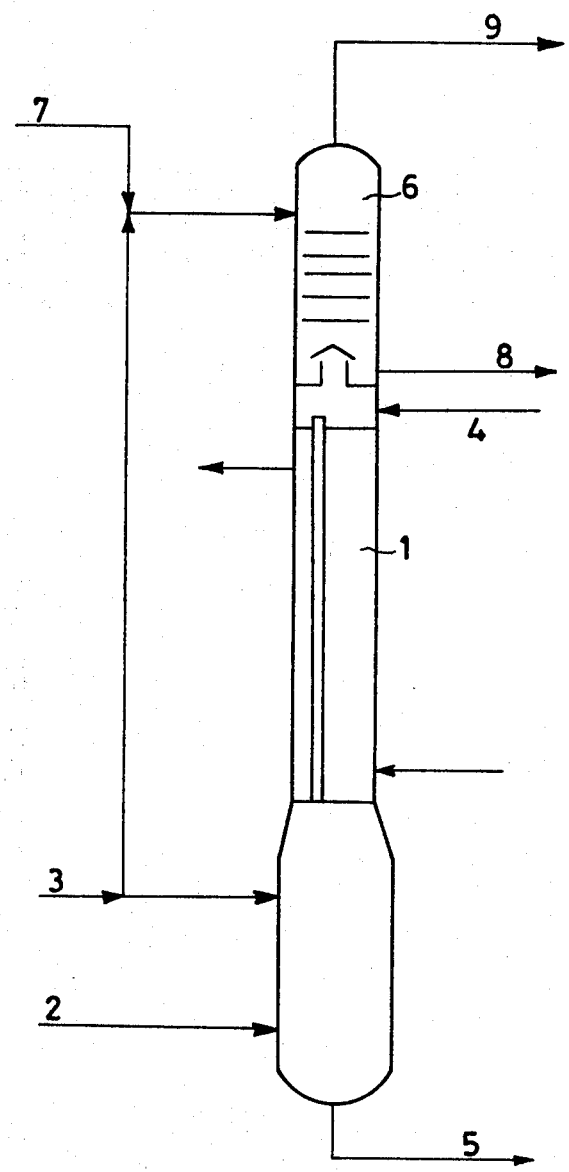

COMBINED PROCESS FOR THE PRODUCTION OF UREA AND AMMONIA

CROSS-REFERENCE TO RELATED APPLICATION

This application is a continuation of application Ser. No. 880,139, filed Feb. 22, 1978, now abandoned.

This invention relates to a combined process for the production of urea and ammonia.

More detailedly, the present invention relates to an integrated urea-ammonia production process which is improved under the respect of the absorption of carbaon dioxide in the zone of formation of the ammonium carbamate.

It is known from the Italian Patent Specification No. 907 469 that the absorption of the $CO_2$ contained in the raw gases for the synthesis of ammonia is carried out with an ammoniacal aqueous solution in a film-exchanger, the aqueous ammoniacal solution being fed both at the bottom and at the top of such film-type heat exchanger.

Regrettably, during the absorption step, the evaporation of about the 20% of ammonia takes place, so that such ammonia must partially be condensed and fed back to the $CO_2$-absorption apparatus. The remaining fraction of ammonia which is still contained in the gases emerging from the $CO_2$-absorption zone, which is the zone in which ammonium carbamate is formed, is sent, on completion of the partial condensation mentioned, just now, to the ammonia-absorber, wherein such ammonia is absorbed, along with the ammonia which comes from the ammonia-synthesis apparatus, with water.

Processing cycle complications and considerable expenditures involved when working by absorbing $CO_2$ according to the conventional art resumed above have been done away with by the method according to the present invention.

An object of the present invention is to provide a process for the production of urea, combined with the production of ammonia, according to which the absorption of the $CO_2$ contained in the raw gases intended for the synthesis of ammonia is carried out by introducing said $CO_2$-containing gases at the bottom, or in the vicinity of the bottom, of an absorber, the latter being split into two sections, i.e. the lower section of the film-type, and the upper section of the plate-type.

The other operations of the combined process are the known ones, and essentially consist in producing ammonia in a synthesizing apparatus for ammonia, absorbing the ammonia, as it emerges from the synthesizing reactor, with water so as to obtain a concentrated ammonia solution to be used for absorbing the $CO_2$ contained in the raw gases for the synthesis of ammonia, absorbing the $CO_2$ according to the teachings of the present invention and forming ammonium carbamate, partially converting the ammonium carbamate into urea in a urea-synthesis reactor, thermally decomposing the unconverted carbamate into urea and stripping the decomposition products with a gas selected from among ammonia, $CO_2$ or inerts, ammonia being preferred, dumping from the stripping zone a solution of urea which still contains carbamate values, recycling the carbamate decomposition products to the urea-synthesis reactor, distilling under a pressure of from 3 to 30 atmospheres, in one or more stages, the solution of urea, there being obtained in this way liquid ammonia and one or more ammoniacal solutions of ammonium carbonate on the one side, and, finally, an ammonium-carbamate-free aqueous solution of urea on the other side.

Carbon dioxide is then absorbed in two discrete sections of the same apparatus.

More particularly, the main fraction of the $CO_2$ is absorbed in the section which is equipped with tubes, wherein the absorbing solution, which is an ammoniacal solution of ammonium carbonate as obtained by distillation of the solution of urea under a low pressure after that the major fraction of the ammonium carbamate has been withdrawn under a pressure substantially equal to the synthesizing pressure, smoothly runs along the tube walls in the form of a thin film, the absorption heat being removed by the agency of a coolant fluid which flows outside the tube walls. The remaining portion of $CO_2$ is removed in the plate section, which is essentially adiabatic, the absorbing fluid being a concentrated ammoniacal aqueous solution.

The pressure under which the urea solution is distilled in order to obtain the ammoniacal solution of ammonium carbonate ranges from 3 to 30 atm.

In the plate absorbing section, liquid ammonia is also used with advantage, concurrently with the concentrated ammoniacal aqueous solution. The preferred weight ratio of liquid ammonia to concentrated ammoniacal aqueous solution ranges from 1 to 5.

The absorbing liquor is fed to the film-type absorption section by means of a distributor which is located in a zone which is intermediate between the two sections.

Likewise, the absorbing liquor (concentrated ammoniacal aqueous solution possibly supplemented by liquid ammonia) is fed to an area placed at the top, or near the top, of the plate absorption section. The solution emerging from the plate section is directly sent to the urea-synthesis reactor: as an alternative, it can flow through the film-absorption section by means of an appropriate distributor and can be distributed in film-form onto the surfaces of the tubes of the film-absorption section together with the ammoniacal solution of ammonium carbonate which is directly fed to the film-absorption section.

It should be observed that in the film-absorption zone, the $CO_2$ is absorbed to such an extent as to have residual gas values of 2%–3% on a volume basis.

During this stage, a certain evaporation of ammonia takes place, so that the gas deprived of the carbon dioxide has a contents of ammonia equal to about 10%–12% by volume. This gas subsequently enters the second top section, the plate section, wherein, by the scrubbing mentioned above, it becomes possible completely to absorb both the carbon dioxide and the ammonia which are present.

It should be observed that by operating according to the method of this invention, it becomes possible not only to reduce the exchange surfaces which are necessary, but also the work under conditions of great safety on account of the considerable excess of ammonia and the relative thermal volume thereof.

It is possible, according to the present invention, as it is obvious, to absorb the $CO_2$ in two serially arranged absorption sections, that is, sections which are not superposed to one another: in the first section the absorption takes place with the film method, whereas the second section has a set of plates for absorbing the residual $CO_2$ which had not been absorbed in the film-absorption section.

In this case, the raw gas for the synthesis of ammonia, which contains $CO_2$ is fed at the bottom, or near the bottom, of the film-absorption section in which the absorbing liquor (ammoniacal solution of ammonium carbonate) is fed at the top, or near the top, of said section, whereas the gas discharged from the top of the film-absorption section is fed at the bottom, or near the bottom, of the plate-absorption section: the absorbing liquor consisting of the concentrated ammoniacal aqueous solution, possibly supplemented by liquid ammonia, is conversely fed at the top of the plate section. The gas, deprived of its $CO_2$, is discharged from the top of the plate-absorption section, whereas the solution as obtained at the bottom of the plate section can, if desired and with advantage, be exploited as an additional absorbing liquor in the film-absorption section.

An example will now be given, which is intended for better illustrating the invention without limiting it in any wise:

PRACTICAL EXAMPLE

To produce 1,000 metric tons an hour of urea, there is fed at the bottom of the absorber 1, shown in the accompanying diagram and which works under a pressure of 195 kg/sq.cm, a raw gas 2 having the following percentage composition, by volume:

| Ar | 215 | nor. cu. meters an hour | 0.24% | by volume |
|---|---|---|---|---|
| $H_2$ | 55,425 | " | 61.52% | " |
| $N_2$ | 18,161 | " | 19.99% | " |
| $CH_4$ | 251 | " | 0.28% | " |
| CO | 390 | " | 0.43% | " |
| $CO_2$ | 15,804 | " | 17.54% | " |

The working temperature is 175° C.

At 3 the following ammoniacal solution, having a temperature of 50° C., is introduced:

| $NH_3$ | 25,370 kg an hour | 80% by weight |
|---|---|---|
| $H_2O$ | 6,343 kg an hour | 20% by weight |
| total | 31,713 kg an hour | |

At the top portion of the film absorber 1, the recycle carbonate, proceeding from 4, is fed at a temperature of 103° C.

| $NH_3$ | 5,558 | kg an hour | 26.75% | by weight |
|---|---|---|---|---|
| $CO_2$ | 7,076 | " | 34.24% | " |
| $H_2O$ | 8,059 | " | 39.01% | " |
| total | 20,663 | " | 100.00% | " |

The concentrated solution of carbamate exits the bottom and shall be sent to the urea reactor 5, at the temperature of 140° C.

| $NH_3$ | 24,834 | kg an hour | 35.43% | by weight |
|---|---|---|---|---|
| $CO_2$ | 31.343 | " | 44.71% | " |
| $H_2O$ | 13,920 | " | 19.86% | " |
| total | 70,097 | " | 100.00% | " |

From the film section the gas, partially stripped of its $CO_2$ emerges and is sent at a temperature of 125° C. to the plate section 6:

| Ar | 215 | nor.cu.meters an hour | 0.25% | by volume |
|---|---|---|---|---|
| $H_2$ | 55,425 | " | 63.44% | " |
| $N_2$ | 18,161 | " | 20.78% | " |
| $CH_4$ | 251 | " | 0.29% | " |
| CO | 390 | " | 0.45% | " |
| $CO_2$ | 3,451 | " | 3.95% | " |
| $NH_3$ | 9,467 | " | 10.84% | " |
| total | 87,360 | " | 100.00% | " |

The absorption heat is withdrawn from the jacket side of the absorber, to produce low-pressure steam.

At the top of the plate section, there are fed:

Ammoniacal solution (temperature 50° C.), from 3:

| $NH_3$ | 12,684 kg an hour | 80% by weight |
|---|---|---|
| $H_2O$ | 3,172 kg an hour | 20% by weight |

Recycled anhydrous ammonia, at a temperature of 38° C., from 7: 35,874 kg an hour.

From the bottom of the plate section, the following solution emerges via 8 at the temperature of 117° C.:

| $NH_3$ | 45,939 | kg an hour | 82.20% | by weight |
|---|---|---|---|---|
| $CO_2$ | 6,778 | " | 12.13% | " |
| $H_2O$ | 3,172 | " | 5.67% | " |
| total | 55,889 | " | 100.00% | " |

Such solution is sent to the urea-synthesis reactor.

From the top of the plate section the $CO_2$-stripped gas emerges via 9 at a temperature of 43° C.:

| Ar | 215 | nor.cu.m an hour | 0.25% | by volume |
|---|---|---|---|---|
| $H_2$ | 55.425 | " | 63.44% | " |
| $N_2$ | 18,161 | " | 20.79% | " |
| $CH_4$ | 251 | " | 0.29% | " |
| CO | 390 | " | 0.45% | " |
| $NH_3$ | 12,918 | " | 14.78% | " |
| total | 87,360 | " | 100.00% | " |

This gas is sent to methanization.

We claim:

1. In a method for the concurrent production of ammonia and urea comprising the steps of producing ammonia in an ammonia-synthesis apparatus, absorbing ammonia at the exit of the ammonia-synthesis reactor with water, thus obtaining a concentrated aqueous solution of ammonia, utilizing the concentrated solution of ammonia for the absorption of the $CO_2$ contained in the raw gases for the synthesis of ammonia, obtaining ammonium carbamate, converting the ammonium carbamate partially into urea in a urea-synthesis reactor, thermally decomposing the carbamate which has not been converted into urea and stripping the decomposition products with a gas selected from the group consisting of ammonia, $CO_2$ and inerts, discharging from the stripping zone a solution of urea which still contains carbamate, recycling the products of decomposition of the carbamate to the urea-synthesis reactor, distilling under a pressure of from 3 to 30 atm, in at least one stage, the solution of urea to obtain liquid ammonia and one or more ammoniacal solutions of ammonium carbonate, and an aqueous solution of urea deprived of ammonium carbamate the improvement which comprises introducing the $CO_2$-containing gas at the bottom, or near the bottom, of an absorber which is split into two sections, the lower section being a film-absorber and the upper section being a plate-absorber, the absorbing solution in the upper section being the concentrated aqueous solution of ammonia aforesaid, the absorbing solution in the lower section being one or more of the aqueous ammoniacal solutions of ammonium carbonate as obtained by distillation of the solution of urea under a pressure of from 3 to 30 atm. with addition of liquid ammonia.

2. A combined process according to claim 1 wherein the film absorption section and the plate absorption section are arranged serially, the raw gas which contains $CO_2$ being fed at the bottom, or near the bottom, of the film absorption system, then discharged from the top of such film absorption section and fed into the bottom, or near the bottom, of the plate absorption section, the absorbing liquor for the film absorption section fed at the top or near the top of such section being composed of said one or more ammoniacal solutions of ammonium carbonate, the absorbing liquor for the plate absorption section fed at the top or near the top thereof being composed of the concentrated aqueous solution of ammonia.

3. The process of claim 2 wherein said one or more ammoniacal solutions of ammonium carbonate are supplemented by liquid ammonia.

4. The process of claim 2 wherein said plate absorption section is supplemented by the solution as obtained from the bottom of the plate absorption section.

5. A process as claimed in claim 1 wherein said stripping gas for said decomposition products is ammonia.

6. A process as claimed in claim 1 wherein said distillation of the solution of urea under a pressure of from 3 to 30 atm. is effected without addition of liquid ammonia.

7. A combined process according to claim 1 wherein the weight ratio of the liquid ammonia to said one or more solutions of ammonium carbonate ranges from 1 to 5.

* * * * *

UNITED STATES PATENT AND TRADEMARK OFFICE
CERTIFICATE OF CORRECTION

PATENT NO. : 4,291,006
DATED : September 22, 1981
INVENTOR(S) : Giorgio Pagani, Vincenzo Lagana & Francesco Saviano It is certified that error appears in the above—identified patent and that said Letters Patent is hereby corrected as shown below:

Page 1, under section [30], insert:

Foreign Application Priority Data

March 3, 1977 [IT] Italy .................... 20850 A/77

*Signed and Sealed this*

*Twenty-third* Day of *March 1982*

|SEAL|

Attest:

GERALD J. MOSSINGHOFF

*Attesting Officer*     *Commissioner of Patents and Trademarks*